United States Patent
Ditzel et al.

(10) Patent No.: US 8,692,015 B2
(45) Date of Patent: Apr. 8, 2014

(54) CARBONYLATION PROCESS

(75) Inventors: Evert Jan Ditzel, East Yorkshire (GB); Bogdan Costin Gagea, Hull (GB)

(73) Assignee: BP Chemicals Limited, Middlesex (GB)

( * ) Notice: Subject to any disclaimer, the term of this patent is extended or adjusted under 35 U.S.C. 154(b) by 209 days.

(21) Appl. No.: 13/138,987

(22) PCT Filed: May 6, 2010

(86) PCT No.: PCT/GB2010/000917
§ 371 (c)(1),
(2), (4) Date: Nov. 9, 2011

(87) PCT Pub. No.: WO2010/130973
PCT Pub. Date: Nov. 18, 2010

(65) Prior Publication Data
US 2012/0053360 A1 Mar. 1, 2012

(30) Foreign Application Priority Data
May 14, 2009 (EP) .................................... 09251310

(51) Int. Cl.
*C07C 67/36* (2006.01)
*C07C 67/37* (2006.01)

(52) U.S. Cl.
USPC ............................ 560/232; 562/517; 562/519

(58) Field of Classification Search
CPC ....................................................... C07C 67/36
USPC .................................... 560/232; 562/517, 519
See application file for complete search history.

(56) References Cited

U.S. PATENT DOCUMENTS

| | | | |
|---|---|---|---|
| 3,619,412 A | 11/1971 | Clement et al. | |
| 4,039,479 A | 8/1977 | Gembicki et al. | |
| 5,118,482 A | 6/1992 | Narayana et al. | |
| 2012/0078005 A1* | 3/2012 | Armitage et al. | 560/232 |
| 2012/0101298 A1* | 4/2012 | Ditzel et al. | 560/206 |

FOREIGN PATENT DOCUMENTS

| | | |
|---|---|---|
| EP | 1 985 362 A1 | 10/2008 |
| WO | WO 2008/147190 A1 | 12/2008 |

OTHER PUBLICATIONS

PCT International Preliminary Report on Patentability; International Application No. PCT/GB2010/000917; filed May 6, 2010 (7 pgs).

* cited by examiner

*Primary Examiner* — Yong Chu
(74) *Attorney, Agent, or Firm* — Nixon & Vanderhye P.C.

(57) ABSTRACT

Process for the production of at least one carbonylation product selected from acetic acid and methyl acetate, by carbonylating at least one carbonylatable reactant selected from methanol and reactive derivatives thereof with carbon monoxide in the presence of a catalyst. The catalyst is a mordenite which has been treated with an aqueous ammonium hydroxide solution and has a silica:alumina molar ratio of at least 10:1, and the reactive derivatives are selected from methyl acetate and dimethyl ether.

15 Claims, 1 Drawing Sheet

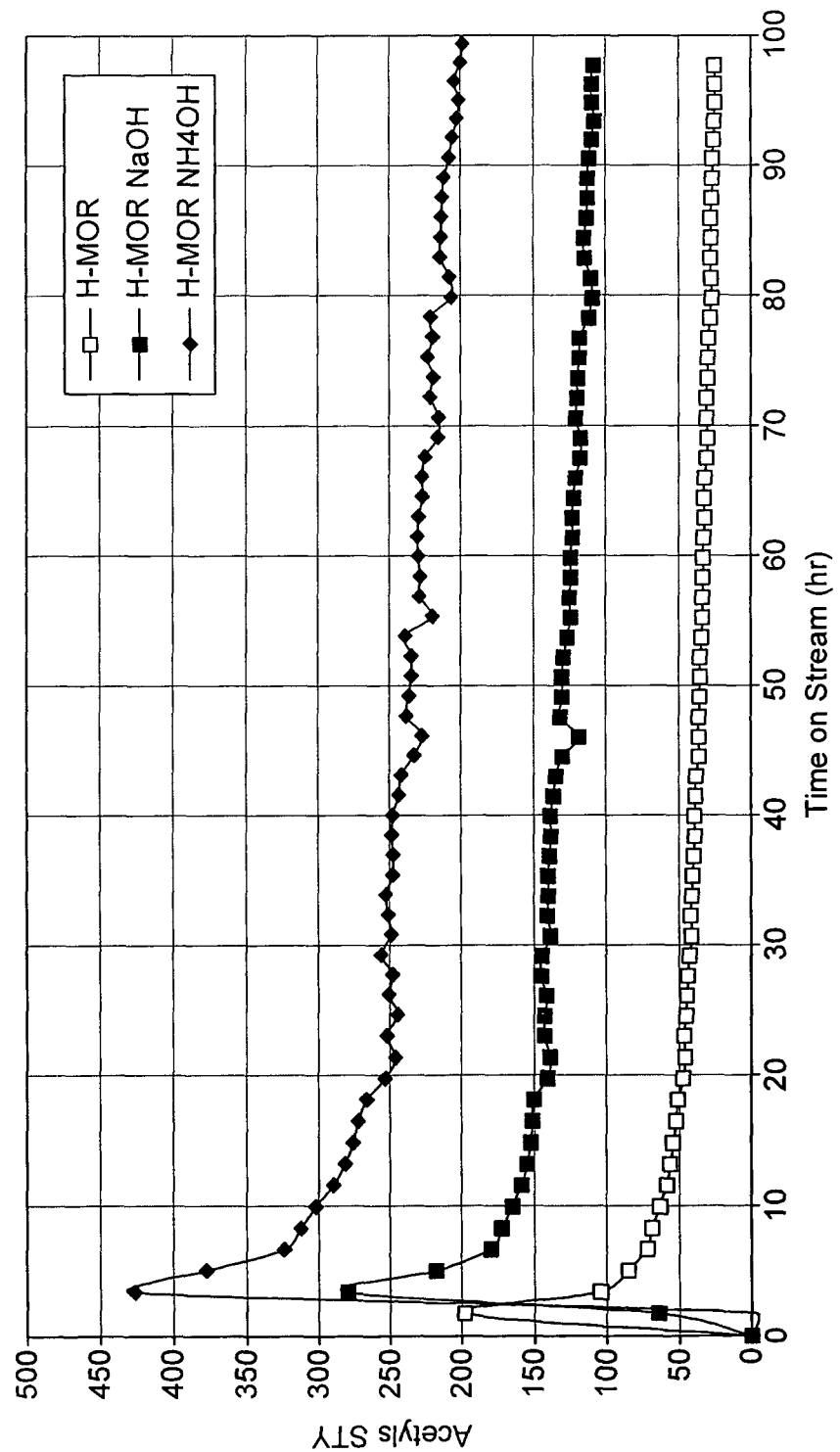

CARBONYLATION PROCESS

This application is the U.S. national phase of International Application No. PCT/GB2010/000917 filed 6 May 2010 which designated the U.S. and claims priority to European Application No. 09251310.0 filed 14 May 2009, the entire contents of each of which are hereby incorporated by reference.

This invention relates to a process for the carbonylation of methanol and/or reactive derivatives thereof with carbon monoxide to produce acetic acid and/or methyl acetate in the presence of an improved mordenite carbonylation catalyst. In particular, the invention relates to a process for the carbonylation of methanol and/or reactive derivatives thereof with carbon monoxide to produce acetic acid and/or methyl acetate in the presence of a mordenite catalyst of improved carbonylation catalytic activity.

BACKGROUND OF THE INVENTION

Zeolites are microporous crystalline structures that are widely applied as catalysts in the petroleum and chemical industries. Transport of molecules through zeolitic micropores occurs by diffusion and is believed to affect the rate of a reaction. However, the microporous network limits diffusion, hindering access to the active sites and limiting the reaction rate. Attempts have been made to improve catalytic effectiveness by the introduction of mesoporosity into the micropore structure. Mesopores provide improved access to the micropores thereby enhancing the rate of diffusion and thus the catalytic performance.

An effective method of increasing mesoporosity in zeolites has proven to be the selective extraction of silicon from a zeolite framework, referred to in the art as desilication. The use of desilication to increase the mesoporosity of mordenite, is for example, described in WO 2008/147190. In WO 2008/147190, a mesoporous mordenite is prepared by subjecting a non-dealuminated mordenite having an atomic ratio of framework Si to Al of at least 15, to an alkaline treatment, such as sodium hydroxide, in order to create mesoporosity by removal of silicon.

U.S. Pat. No. 5,118,482 describes a process for realuminating zeolites, thereby reducing their silica alumina ratio whereby the framework aluminium content of a framework deficient zeolite containing non-framework aluminium is increased by contacting the zeolite with an aqueous basic solution at a temperature greater than about 25° C.

Zeolites, such as mordenite are known to catalyse hydrocarbon conversion reactions, such as hydrocracking and the transalkylation of hydrocarbons. For example, U.S. Pat. No. 3,619,412 describes the preparation of a hydrocracking catalyst by impregnating a support consisting of a mixture of mordenite and amorphous silica-alumina with a solution of a fluorine compound, drying and treating with a solution containing one or more hydrogenative metals. U.S. Pat. No. 4,039,479 describes a method of manufacturing a catalytic composite by subjecting a mordenite with a sodium content of less than 5 wt % as $Na_2O$ to an aqueous ammoniacal treatment at a pH of at least about 9.5, calcining in intimate admixture with a non-zeolitic refractory inorganic oxide, such as alumina and a metal salt convertible to said oxide at calcination conditions, such as aluminium salts. It is stated that the inclusion of the metal salt in admixture with the zeolite and refractory inorganic oxide has been found to effect a significant improvement in the activity of the catalytic composite produced therefrom, particularly with respect to the transalkylation of alkylaromatic hydrocarbons.

Carbonylation processes for the production of acetic acid and/or methyl acetate by carbonylating methanol and/or reactive derivatives thereof with carbon monoxide are known. Such processes typically employ Group VIII metal catalysts, such as rhodium and iridium. Mordenites are also known to catalyse carbonylation reactions. For example, there is described in EP-A-1 985 362 a process for the carbonylation of dimethyl ether in the presence of a mordenite catalyst. In EP-A-1 985 362 it was found that improved catalytic activity could be achieved by using a mordenite catalyst which had been loaded with silver and/or copper and also a low level of platinum.

SUMMARY OF THE INVENTION

It would be desirable to find an alternative method of improving the catalytic performance of mordenite in the carbonylation of methanol and/or reactive derivatives thereof, and, in particular a method which also avoids or mitigates the use of promoter metals.

It has now been found that the catalytic activity of mordenite in carbonylation reactions can be improved by treating a mordenite with an aqueous solution of ammonium hydroxide.

Accordingly, the present invention provides a process for the production of at least one carbonylation product selected from acetic acid and methyl acetate which process comprises carbonylating at least one carbonylatable reactant selected from methanol and reactive derivatives thereof with carbon monoxide in the presence of a catalyst, wherein said catalyst is a mordenite which has been treated with an aqueous ammonium hydroxide solution and has a silica:alumina molar ratio of at least 10:1.

The catalyst for use in the carbonylation process of the present invention is a mordenite which has been subjected to a treatment with an aqueous solution of ammonium hydroxide.

It has been found that in the carbonylation of methanol and/or reactive derivatives thereof the catalytic activity of a mordenite treated with aqueous ammonium hydroxide solution is significantly improved compared to the catalytic activity in the carbonylation reaction of an untreated mordenite. This finding is contrary to expectations. Mordenites treated with alkali metal hydroxides, such as sodium hydroxide, have improved catalytic activity due to the base treatment inducing a significant increase in mesoporosity through desilication. However, it has now been discovered that treating a mordenite with ammonium hydroxide solution does not lead to any significant desilication and causes little, if any, change to the mesopore volume. Thus, it would be expected that treating a mordenite with ammonium hydroxide would not alter its catalytic activity and furthermore, it would not be expected that a mordenite treated with ammonium hydroxide would have a higher catalytic activity than the same mordenite treated with an alkali metal hydroxide. Surprisingly, it has been found that mordenites treated with aqueous ammonium hydroxide solution exhibit a superior catalytic activity to mordenites treated with an aqueous sodium hydroxide solution.

The structure of mordenite is well-known and is defined, for example, in The *Atlas of Zeolite Framework Types* (C. Baerlocher, W. M. Meier, D. H. Olson, 5$^{th}$ ed. Elsevier, Amsterdam, 2001). The web-based version (http://www.iza-structure.org/databases/) is a compendium of topological and structural details about zeolites including mordenite.

Mordenite is a naturally occurring zeolite but can be synthesised and obtained commercially. Commercially available forms of mordenite include the sodium form, the acid form and the ammonium form. The mordenite to be treated with aqueous ammonium hydroxide solution may be any form of mordenite, but is preferably the H-form (acid form) or the ammonium form.

Prior to being treated with the aqueous ammonium hydroxide solution, the mordenite may be a mordenite which has been dealuminated to produce a dealuminated mordenite. By a dealuminated mordenite is meant a mordenite which has had aluminium removed from its framework. Dealumination methods are known in the art and include treatment for example, by means of steam and/or acid leaching. Suitable dealumination methods are described, for example in, U.S. Pat. No. 3,551,353 which describes a process for the dealumination of mordenite by contact with steam and mineral acid in alternate steps.

Preferably, the mordenite to be treated with aqueous ammonium hydroxide solution is a dealuminated mordenite.

The mordenite to be treated may have a silica:alumina ratio of at least 10:1, such as in the range 10 to 250:1. Suitably, the silica:alumina ratio of the mordenite is in the range 10 to 100:1, for example, in the range 15 to 60:1, such as 30 to 50:1.

Suitably, the mordenite is treated with an aqueous ammonium hydroxide solution having a pH of 11 or above. The pH of the ammonium hydroxide solution is dependent upon the concentration of ammonia therein. Suitably, ammonia is present in solution in sufficient concentration to provide a pH of 11 or above, such as a pH in the range 11 to 14. Typically, a solution of ammonia in water in which the concentration of ammonia is in the range 15 to 25 wt % may be used.

The temperature and time for which the treatment with the ammonium hydroxide solution is carried out can be varied. However, given that the treatment is carried out in the liquid phase, the temperature chosen for the treatment should be such that an effective concentration of ammonium hydroxide is maintained in solution. Suitably, the temperature may be in the range 70 to 100° C., such as 80 to 90° C. However, lower temperatures, such as temperatures of 50° C. and below may also be employed. For any given treatment level, the required duration of the treatment will be temperature dependent. Treatment at lower temperatures will necessitate a longer duration than treatments carried out at higher temperatures.

The duration of the treatment will depend upon the temperature employed, the concentration of ammonium hydroxide and the physical and chemical characteristics of the mordenite to be treated, and in particular, its silica:alumina molar ratio. However, it has been found that an effective treatment may be carried out by treating a mordenite of silica:alumina molar ratio in the range 15 to 60:1, for example, 30 to 50:1, with ammonium hydroxide solution (15-25 wt % ammonia) at a temperature in the range 70 to 90° C. for several hours, such as at least 5 hours, for example 5 to 24 hours.

Following treatment with ammonium hydroxide solution, the mordenite is suitably filtered off and washed with water to remove any excess ammonium hydroxide and then dried. The ammonium mordenite may be used as catalyst in the process of the present invention or may be, and is preferably, converted to the H-form by, for example a heat treatment method such as calcination.

Advantageously, the treatment of a H- or $NH_4$ form of a mordenite of silica:alumina ratio of 15 to 60:1, such as 30 to 50:1, with ammonium hydroxide solution can be carried out under the conditions of a temperature in the range 50 to 100° C., preferably 80 to 90° C., a pH of the ammonium hydroxide solution in the range 11 to 14, for a duration of 5 to 24 hours, preferably, 5 to 10 hours.

Subsequently, the reaction is quenched and cooled, for example, by submersion of the vessel in an ice-water mixture, followed by filtration and washing with deionised water. After filtration and washing, the mordenite is dried and calcined. Drying is typically carried out at about 110° C. Calcination may be carried out at a temperature sufficient to effect decomposition of the ammonium ions and formation of the H-form of the mordenite. Suitably calcination is carried out at a temperature of at least 400° C., such as in the range 400 to 600° C., for example 450 to 550° C. and may also be carried out under static air.

It has been found that by treating a mordenite with an aqueous ammonium hydroxide solution the silica:alumina ratio of the mordenite prior to treatment remains essentially unchanged. Thus improved catalytic activity in carbonylation processes can be achieved without the need to reduce the silica:alumina molar ratio of a mordenite.

The silica:alumina ratio of a treated mordenite for use as catalyst in the process of the present invention is at least 10:1, for example, in the range 10 to 250:1, suitably in the range 15 to 100:1, such as in the range 25 to 60:1, for example 30 to 50:1.

Thus, the present invention further provides for the use of a catalyst which is a mordenite of silica:alumina ratio of at least 10:1 which mordenite has been treated with an aqueous ammonium hydroxide solution to provide improved catalytic activity in a process for the production of at least one carbonylation product selected from acetic acid and methyl acetate which process comprises carbonylating at least one carbonylatable reactant selected from methanol and reactive derivatives thereof with carbon monoxide.

The catalyst for use in the process of the present invention may be a treated mordenite which is in the ammonium form or preferably, in the H-form. Typically, hydrogen ions are exchanged for ammonium ions on treating the H-form of mordenite with ammonium hydroxide solution. A mordenite in the ammonium form may be converted to the H-form by a heat treatment, such as calcination, to effect thermal decomposition of the ammonium ions and formation of the H-form of the mordenite. Calcination may be carried out at a temperature of at least 400° C., such as in the range 400 to 600° C., for example 450 to 550° C.

The catalyst may be employed in the process of the present invention in any suitable form such as powders, pellets or other forms of extrudates.

The catalyst may be combined with a binder material. Any suitable binders may be employed. Particularly useful binders are inorganic oxide materials such as one or more of the group selected from silica, alumina, silica-alumina, magnesium silicate and magnesium aluminium silicate, preferably, alumina or silica-alumina. Examples of suitable aluminas include boehmite type alumina and gamma-alumina.

Preferably, a binder is a refractory inorganic oxide such that the inorganic oxide is stable at high temperature, and, in particular is stable at temperatures which may be employed in calcination of the catalyst, such as a temperature of at least 400° C., for example, a temperature in the range 400 to 550° C.

Suitable binders may be mesoporous, for example inorganic oxides having a mesoporosity in the range 1 to 500 $m^2/g$. By mesoporosity is meant the sum of the total surface area of mesopores and the external surface area of the binder as measured by nitrogen BET. A mesopore is a pore having a diameter in the range 2 to 50 nanometers.

Preferably, mesoporous binders will also have low microporosity, such as a microporosity in the range 1 to 100 $m^2/g$, preferably in the range 1 to 10 $m^2/g$. By microporosity is meant the sum of the total surface area of micropores and the external surface area of the binder as measured by nitrogen BET. A micropore is a pore having a diameter of less than 2 nanometers.

Suitably, a binder may be present in an amount in the range of 10% to 80% by weight of the catalyst, preferably, in the range of 20% to 65% by weight of the catalyst, and, more preferably, in an amount in the range 35 to 65% by weight of the catalyst.

Suitably, the catalysts for use in the process of the present invention may be combined with a binder which is a refractory inorganic oxide selected from one or more of silica, alumina and silica-alumina, which inorganic oxide is mesoporous, and preferably, an inorganic oxide having a mesoporosity in the range 50 to 500 m2/g.

In the process of the present invention methanol and/or a reactive derivative thereof is carbonylated with carbon monoxide. Reactive derivatives of methanol which may be used as an alternative to, or in addition to methanol, include methyl acetate and dimethyl ether. A mixture of methanol and a reactive derivative thereof, for example a mixture of methanol and methyl acetate, may be employed. Where dimethyl ether is the carbonylatable reactant, it may be generated in-situ from a suitable source, such as dimethyl carbonate. For example, liquid dimethyl carbonate may be contacted with gamma-alumina to decompose the dimethyl carbonate to dimethyl ether and carbon dioxide.

Depending on the nature of the carbonylatable reactant used, the process may be carried out under hydrous or substantially anhydrous conditions. Preferably, where methyl acetate is used as the carbonylatable reactant, the process is carried out in the presence of water. Water may be present in the feed at a molar ratio of methyl acetate:water in the range 50:1 to 2:1. Where the carbonylatable reactant is dimethyl ether, water has been found to inhibit the carbonylation process, thus it is preferred that when using these reactants, the process is carried out under substantially anhydrous conditions. By 'substantially anhydrous' is meant that, in the process, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate product. Suitably, water may be present in the carbonylatable reactant gaseous feed(s) to the reactor in an amount of less than 2.5 wt %, for example, less than 0.5 wt % relative to the amount of dimethyl ether.

The purity of the carbon monoxide used is not deemed to be especially critical although it is desirable to use gas mixtures in which carbon monoxide is the main component. The presence of small amounts of impurities such as nitrogen and the noble gases can be tolerated. The carbon monoxide may be used in admixture with hydrogen. Suitably, the ratio of $CO:H_2$ is in the range 1:3 to 15:1 on a molar basis, such as 1:1 to 10:1. For example, mixtures of carbon monoxide and hydrogen as produced by the reforming or partial oxidation of hydrocarbons (synthesis gas) may also be used in the process of the present invention.

The process of the present invention is preferably carried out by passing methanol vapour and/or dimethyl ether vapour and carbon monoxide gas, optionally in the presence of hydrogen, through a fixed or fluidised bed of catalyst maintained at the desired temperature and pressure.

The process may suitably be carried out at a temperature in the range of 100° C. to 400° C., such as 150 to 350° C.

The process may be carried out at a pressure in the range 1 to 100 barg, such as 10 to 100 barg.

The molar ratio of carbon monoxide to carbonylatable reactant is suitably in the range 1:1 to 99:1, such as 1:1 to 60:1.

Hydrogen may be present in the process, and may be present at a partial pressure of at least 0.1 barg, such as 1 to 30 barg.

The Gas Hourly Space Velocity (GHSV) is suitably in the range 500 to 40,000 $h^{-1}$, such as 2000 to 10,000 $h^{-1}$.

Prior to use in the process, the catalyst is activated by, for example, by subjecting it to elevated temperature for at least one hour under flowing nitrogen, carbon monoxide or hydrogen.

If desired, the carbonylatable reactant may be contacted with a bed of alumina or corundum immediately before the bed of catalyst.

Preferably, the process of the present invention is carried out substantially in the absence of halides, such as iodide. By substantially is meant that the halide content, such as the iodide content of the feed gases and catalyst are less than 500 ppm and preferably less than 100 ppm.

The process may be carried out either as a fixed bed, fluid bed or moving bed process.

The process may be operated as either a continuous or a batch process, preferably as a continuous process.

The product of the process is acetic acid and/or methyl acetate. Where the carbonylatable reactant is methanol, the carbonylation product is acetic acid but methyl acetate may also be produced, depending on the extent of carbonylation.

Where the carbonylatable reactant is dimethyl ether the primary product of the process is methyl acetate but small amounts of acetic acid may also be produced.

The acetic acid produced by the process can be removed in the form of a vapour and thereafter condensed to a liquid. The acetic acid can be subsequently purified using conventional techniques, such as distillation.

Where methyl acetate is a product of the process, at least some may be recovered from the carbonylation reaction products and sold as such and/or recycled to the carbonylation reactor and/or at least a portion may be recovered and used as such as a feedstock for other chemical processes, and/or at least a portion of it may be hydrolysed to acetic acid using known techniques such as reactive distillation in the presence of an acid catalyst.

BRIEF DESCRIPTION OF THE DRAWINGS

In the Figures, FIG. 1 depicts space time yield (STY) to acetyls (acetic acid and methyl acetate) carbonylation products (g/l/h) versus time on stream (hours) using H-mordenite and H-mordenites treated with sodium hydroxide or ammonium hydroxide as catalyst in the carbonylation of dimethyl ether.

The invention will now be illustrated with reference to the following Examples.

EXAMPLE 1

Catalyst Preparation
Catalyst A
Catalyst A was a H-mordenite of silica:alumina ratio of 40.5 supplied by BASF
Catalyst B: Catalyst a Treated with Sodium Hydroxide
An alkaline solution (1.5 L of aqueous NaOH 0.2M) was heated to 65° C. with vigorous stirring. After the system reached equilibrium, 50 g of Catalyst A was added and stirred continuously for 30 minutes. After 30 minutes, the suspension was cooled in ice cold water under stirring. The mixture was then filtered under vacuum, washed with 3 liter deionised water and dried overnight at 110° C. in an air oven. The base treated mordenite was exchanged 3 times with an aqueous solution of NH₄NO₃ (10 ml/g of mordenite, 1M) at 80° C. for a period of 1 hour. Following each exchange step the NH₄-mordenite was washed with deionised water. The wet NH₄-mordenite was dried at 110° C. and then converted to the H-form of the mordenite using calcination method I below.

Catalyst C: Catalyst a Treated with Ammonium Hydroxide

Ammonia solution (90 ml of aqueous NH₃, 25 wt %, pH 13.5) was added to 5 g of Catalyst A loaded in a 100 ml stainless steel autoclave. The autoclave was then sealed and maintained at a temperature of 85° C. in a rotary oven for 8 hours. The autoclave was cooled in ice cold water and the suspension filtered under vacuum, washed with 0.5 L of deionised water and dried at 110° C. The resulting NH₄-mordenite was calcined using calcination method I to obtain the H-form of the mordenite.

Calcination Method I

Calcination was carried out under static air by heating a mordenite to 90° C. at 3° C./min and holding for 2 hours, heating to 110° C. at 1° C./min and holding for 2 hours, heating to 500° C. at 3° C./min and holding for 3 hours before cooling to room temperature.

Characterisation

Certain physiochemical properties of the Catalysts A to C are given in Table 1.

Subsequently, the sample was heated to 800° C. with a ramp rate of 5° C./min. The desorbed ammonia was captured using a 0.25% boric acid solution which was continually maintained at pH=5 using a Mettler Toledo T50 autotitrator loaded with 0.02M hydrochloric acid.

The % of extra-framework aluminium in a mordenite was determined by solid state $^{27}Al$ NMR. Extra-framework aluminium refers to aluminium which is not located in the framework of the crystal structure of the mordenite but is located elsewhere in the mordenite, such as in the pores and channels.

The silica:alumina molar ratio was determined by inductively coupled plasma atomic emission spectrometry (ICP-OES).

Carbonylation Reactions

A series of carbonylation reactions were carried out using each of Catalysts A to C.

Prior to use, each catalyst was calcined according to the method described in carbonylation method I. Prior to loading into the reactor, 0.75 g of each catalyst was compacted at 12 tonnes in a 33 mm die set using a pneumatic press, and crushed and sieved to a particle size fraction of 250 to 500 microns. A Hastelloy reactor tube was packed with 0.6 ml catalyst and 0.2 g of a pre-bed of gamma alumina. The portion of the reactor tube containing the catalyst was heated by means of an electrical heating jacket. The reactor and heating jacket were themselves mounted in a heated cabinet which

TABLE 1

| | $V_{mesopores}$ (ml/g) | $V_{micropores}$ (ml/g) | $S_{external}$ (m²/g) | $S_{BET}$ (m²/g) | $NH_3$-$TPD_{HT}^a$ (mmol/g) | $Al_{EF}^b$ (%) | Silica:Alumina molar ratio |
|---|---|---|---|---|---|---|---|
| H-MOR (Catalyst A) | 0.1 | 0.18 | 50 | 531 | 0.72 | 13.7 | 40.5 |
| H-MOR NaOH (Catalyst B) | 0.44 | 0.15 | 121 | 497 | 0.70 | 16.6 | 27.5 |
| H-MOR NH₄OH (Catalyst C) | 0.16 | 0.18 | 63 | 521 | 0.74 | 18.7 | 39.8 |

$^a$Desorbed NH₃ in the High Temperature region >300° C.
$^b$Extra-framework aluminium determined by solid state $^{27}Al$ NMR The properties of the three mordenite catalysts were determined using the following analytical techniques. N₂ adsorption was carried out at 77K in a Micromeritics Tristar 3000 apparatus equipped with Tristar 3000 v6.01 software for data analysis. Before the analysis, samples were degassed under vacuum at 60° C. for 30 minutes and then at 120° C. for 16 hours. The BET surface area was derived from data points in the relative pressure range of $p/p_0$=0.01-0.05 based on a published model [S. Brunauer, P. H. Emmett, E. Teller, J. Am. Chem. Soc. 60 (1938) 309]. T-plot method was used to determine the micropore volume and external surface area using a fitted thickness range of 0.35-0.5 nm [B. C. Lippens, J. H. de Boer, J. Catal. 4 (1965) 319]. The mesopore volume was calculated by substracting the micropore volume from the total pore volume (determined using the single point adsorption total pore volume; $p/p_0$>0.98).

Temperature programmed desorption of ammonia (NH₃-TPD) was carried out in a custom built apparatus consisting of a quartz u-tube loaded in a Severn Science Limited furnace. The quantitative ammonia analysis was carried out using a titration method. The sample (50 mg) was pretreated at 100° C. for 30 minutes under a 30 ml/min flow of nitrogen. 1% ammonia in nitrogen was then passed over the sample for 1 hour. Afterwards, a 30 ml/min nitrogen flow was passed over the sample for 1.5 hours to purge any physisorbed ammonia.

maintained the temperature of the pre-bed. The heated cabinet was typically maintained at 130° C. Prior to start-up of the carbonylation reaction, the reactor was heated at atmospheric pressure to 130° C. under a flow of nitrogen. At a temperature of 130° C., a gas comprising 80 mole % carbon monoxide and 20 mole % hydrogen was introduced into the reactor at a flow rate (GHSV) of 5000 per hour, and the reactor pressurised to 20 barg, heated to a temperature of 300° C. and maintained under these conditions for 2 hours. The carbonylation reaction was then started by feeding liquid dimethyl carbonate at a rate designed to give a gas feed comprising 76 mole % carbon monoxide, 19 mole % hydrogen and 5 mole % dimethyl ether. The reaction was allowed to continue for 100 hours under conditions of 300° C., 20 bar, and a gas hourly space velocity (GHSV) of 5000 h⁻¹. A constant flow of reaction off-gases was taken, let down to atmospheric pressure at a temperature of 130° C. and passed to a gas chromatograph for analysis of acetyls products (acetic acid and methyl acetate). The results of the carbonylation reactions are shown in FIG. 1.

FIG. 1 clearly shows that the mordenite treated with either NaOH or NH₄OH showed a much higher catalytic activity than the untreated mordenite. The NaOH treated mordenite was 4 times more active than the untreated mordenite and the NH₄OH treated mordenite was 8 times more active than the untreated mordenite. The NH₄OH treated mordenite was found to be twice as active as the NaOH treated mordenite.

EXAMPLE 2

(i) Catalyst D: Catalyst A Combined with a Binder

Catalyst D was prepared by combining Catalyst A with an alumina binder as follows. 30 g of Catalyst A and 15 g of alumina (ex Sasol, Pural SCF) were gently milled together in a Büchi powder drying flask to produce a free flowing powder. The powder was blended on a rotor evaporator at a speed of 100 r.p.m. for 1 hour at ambient temperature and pressure and then calcined for 3 hours at 500° C. under an atmosphere of static air.

(ii) Catalyst E: Catalyst C Combined with a Binder

Catalyst E was prepared by combining 20 g of Catalyst C with 10 g of alumina binder (ex Sasol, Pural SCF) in accordance with the method described above for Catalyst D.

Carbonylation Reactions using Catalysts D and E

Carbonylation reactions of dimethyl ether with carbon monoxide were performed using Catalyst D and Catalyst E.

Prior to loading in a reactor each catalyst was compacted at 10 tonnes in a 13 mm die set using a pneumatic press, and crushed and sieved to a particle size fraction of 125 to 160 microns.

The carbonylation reactions were carried out in a pressure flow reactor unit consisting of 16 identical reactors of the type described in WO 2005063372. Each reactor had an internal diameter of 9.2 mm and the centre of each reactor was fitted with a tube of diameter 3.2 mm into which a thermocouple was placed.

A 10 cm corundum bed of sieve fraction of 125-160 μm was placed in each reactor. On a dry mass basis (determined by loss on ignition of the catalyst measured by heating the catalyst from room temperature to 600° C. at a ramp rate of 30° C. per minute), 1.948 g (approximately 3 ml) of a catalyst diluted with 3 ml of corundum was placed on top of the corundum bed. The diluted catalyst was covered by 11 cm bed of corundum of particle size of 125-160 microns. 1 g of gamma-alumina (ex BASF SAS 250) of pellet size 125-160 microns was placed on top of the corundum, to a depth of 2 cm.

The reactors were pressurised to a reaction pressure of 70 bar with a gas feed of a 4:1 molar ratio of carbon monoxide: hydrogen at a flow rate of 12 L/h per reactor. The reactors were then heated at 1° C./min to a holding temperature of 220° C., where they were held for a dwell time of 3 hours. The temperature was then ramped to 300° C. at 1° C./min, again followed by a dwell time of 3 hours. The gas feed was then changed to a mixture of carbon monoxide, hydrogen, dimethyl ether, argon and methyl acetate at a molar ratio of 70.8:17.7:6:5:0.5 respectively at a total flow rate of 12 L/h per reactor, with a dimethyl ether vapour feed rate of 0.72 L/h per reactor and a methyl acetate vapour feed rate of 0.06 L/h per reactor. Nitrogen was introduced at a variable rate of 0-150 ml/min to equalise the pressure swings between the 16 reactor exits. The exit stream from each reactor was periodically passed to a gas chromatograph to determine the concentration of reactants and carbonylation products. The reaction was allowed to continue for 263 hours under conditions of 300° C., 70 bar and a gas hourly space velocity (GHSV) of 4000/h.

From the gas chromatography analysis, the space time yield (STY) of acetyls products was calculated as the molar equivalent weight of acetic acid corresponding to the sum of the methyl acetate and acetic acid produced expressed as grams of acetic acid per hour per liter of catalyst. The acetyls product was predominantly methyl acetate. The results are given in Table 2.

TABLE 2

| Catalyst | Acetyls STY (g/l/hr) | | |
| --- | --- | --- | --- |
|  | TOS = 50 h | TOS = 105 h | TOS = 160 h |
| Catalyst D | 198 | 150 | 125 |
| Catalyst E | 272 | 278 | 252 |

TOS = time on stream

The results in Table 2 clearly show that the ammonium hydroxide treated Catalyst E is more catalytically active and stable than the non-treated Catalyst D.

The invention claimed is:

1. A process for the production of at least one carbonylation product selected from acetic acid and methyl acetate, which process comprises carbonylating at least one carbonylatable reactant selected from methanol and reactive derivatives thereof, wherein the reactive derivatives are selected from methyl acetate and dimethyl ether, with carbon monoxide in the presence of a catalyst, wherein said catalyst is a mordenite which has been treated with an aqueous ammonium hydroxide solution and has a silica: alumina molar ratio of at least 10:1.

2. A process according to claim 1 wherein the catalyst has a silica: alumina molar ratio in the range 25 to 60:1.

3. A process according to claim 1 wherein the catalyst is a mordenite which has been dealuminated prior to treatment with the aqueous ammonium hydroxide solution.

4. A process according to claim 1 wherein the catalyst is a mordenite which has been treated with an aqueous ammonium hydroxide solution in which the concentration of ammonia is in the range 15 to 25% by weight.

5. A process according to claim 1 wherein the catalyst is a mordenite which has been treated with an aqueous ammonium hydroxide solution at a temperature in the range 70 to 100° C.

6. A process according to claim 1 wherein the catalyst is H-mordenite.

7. A process according to claim 1 wherein the catalyst is combined with a binder.

8. A process according to claim 6 wherein the binder is a refractory inorganic oxide.

9. A process according to claim 8 wherein the refractory inorganic oxide is selected from the group consisting of at least one of silica, alumina, silica-alumina, magnesium silicate and magnesium aluminium silicate.

10. A process according to claim 7 wherein the binder has a mesoporosity in the range 1 to 500 m²/g.

11. A process according to claim 1 wherein the carbonylatable reactant is a reactive derivative which is dimethyl ether.

12. A process according to claim 1 wherein water is present in the carbonylatable reactant feed in an amount of less than 2.5 wt % relative to the amount of dimethyl ether in the feed.

13. A process according to claim 1 wherein the process is carried out in the presence of hydrogen.

14. A process according to claim 1 wherein the carbonylation product is methyl acetate and at least a portion of the methyl acetate is hydrolysed to acetic acid.

15. Process for the product on of at least one carbonylation product selected from acetic acid and methyl acetate, said process comprising carbonylating at least one carbonylatable reactant selected from methanol and reactive derivatives thereof with carbon monoxide using a catalyst which is a mordenite of silica:alumina ratio of 10-250:1 which has been treated with an aqueous ammonium hydroxide solution to provide improved catalytic activity, wherein the reactive derivatives are selected from methyl acetate and dimethyl ether.

\* \* \* \* \*